(12) United States Patent
Wagner

(10) Patent No.: US 8,133,182 B2
(45) Date of Patent: Mar. 13, 2012

(54) MULTI-DIMENSIONAL TRANSDUCER ARRAY AND BEAMFORMING FOR ULTRASOUND IMAGING

(75) Inventor: Paul Wagner, San Carlos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 665 days.

(21) Appl. No.: 12/207,371

(22) Filed: Sep. 9, 2008

(65) Prior Publication Data

US 2010/0063397 A1    Mar. 11, 2010

(51) Int. Cl.
*A61B 8/00* (2006.01)
*A61B 8/14* (2006.01)
*H04R 19/00* (2006.01)

(52) U.S. Cl. ........ 600/459; 600/437; 310/334; 310/344; 310/365; 310/366

(58) Field of Classification Search .......... None
See application file for complete search history.

(56) References Cited

U.S. PATENT DOCUMENTS

| | | | |
|---|---|---|---|
| 6,381,197 B1 | 4/2002 | Savord et al. | |
| 7,046,497 B1* | 5/2006 | Bonin | 361/290 |
| 2003/0048698 A1 | 3/2003 | Barnes et al. | |
| 2003/0103412 A1 | 6/2003 | Ladabaum et al. | |
| 2004/0160144 A1 | 8/2004 | Daft et al. | |
| 2004/0267134 A1* | 12/2004 | Hossack et al. | 600/459 |
| 2005/0119575 A1 | 6/2005 | Ladabaum et al. | |
| 2005/0124884 A1 | 6/2005 | Bolorforosh et al. | |
| 2005/0200241 A1* | 9/2005 | Degertekin | 310/334 |
| 2005/0203409 A1* | 9/2005 | Frey et al. | 600/459 |
| 2005/0215909 A1 | 9/2005 | Barnes | |
| 2006/0035481 A1 | 2/2006 | Petersen et al. | |
| 2006/0173342 A1 | 8/2006 | Panda et al. | |
| 2007/0167752 A1 | 7/2007 | Proulx et al. | |
| 2007/0229336 A1 | 10/2007 | Liu et al. | |
| 2007/0236374 A1 | 10/2007 | Brueske et al. | |
| 2007/0242567 A1* | 10/2007 | Daft et al. | 367/140 |

OTHER PUBLICATIONS

U.S. Appl. No. 11/903,329, filed Sep. 20, 2007.

* cited by examiner

*Primary Examiner* — Long V. Le
*Assistant Examiner* — Farshad Negarestan

(57) ABSTRACT

The electrodes for a CMUT are split to provide separate transmit and receive bias and alternating current electrodes. The transmit electrodes of different elements are interconnected, such as rows sharing bias and columns sharing transmit alternating signals. The bias is used to select an aperture in elevation, and only a sufficient number of transmit beamformer channels to use the selected aperture are needed. On receive, the full multi-dimensional array may be used with integrated beamformer electronics.

8 Claims, 6 Drawing Sheets

Transmitter arrangement 2D monolithically integrated receiver

MULTI-DIMENSIONAL TRANSDUCER ARRAY AND BEAMFORMING FOR ULTRASOUND IMAGING

BACKGROUND

This invention relates to capacitive membrane ultrasound transducers (CMUTs) or other transducer. In particular, the invention relates to a multi-dimensional transducer.

Two-dimensional ultrasound transducers based on matrix array technology are currently limited to a few thousand elements or less. At operating frequencies equal to or below 3 MHz, this limitation is acceptable. For higher frequency probes (e.g., 5-10 MHz) intended for breast and small parts imaging, acceptable image quality cannot be achieved unless tens of thousands of acoustic elements are available for beamformation. However, tens of thousands of electrical connections from an array to an imaging system may not be possible or may be undesired. As a general rule, the element pitch must be less than or equal to one-half of a wavelength for phased arrays and one wavelength for linear arrays in order to achieve good image quality. Therefore, when the frequency is doubled, the wavelength is cut in half and four times as many elements are required for a transducer of the same size.

CMUTs may allow manufacture of arrays with tens of thousands of elements. CMUTs generate and receive ultrasound energy. An array of membranes with respective evacuated cavities between the membrane on the surface of a silicon wafer and the silicon substrate (e.g., cells) are fabricated on silicon wafers using semiconductor processing techniques. Electrodes are deposited on the membrane and the opposing face of the cavity under the membrane. These two electrodes form a capacitor. When the capacitor is charged electrically (or electrically biased), electrostatic forces pull the membrane toward the substrate electrode. In this state, changing the voltage on the capacitor modulates the electrostatic force on the membrane and causes the membrane to move up or down. In a reciprocal fashion, forcing the charged membrane to move up and down changes the voltage on the capacitor.

CMUTs offer many advantages over traditional ceramic transducers. For example, electrostatic transducers may be cheaper to manufacture, allow higher manufacturing yields, provide more size and shape options, use non-toxic materials, and have higher bandwidth. However, electrostatic transducers require a bias voltage for operation. The bias voltage in combination with any transmit voltage is limited to avoid collapse of the membrane. The electrostatic attraction of the membrane cannot exceed the restoring spring force of the membrane. Likewise, the dielectric breakdown of the gap between electrodes is usually avoided.

Another advantage is a reduction in the number of connections to an imaging system. Monolithically integrated receive electronics incorporating partial beamformation, data multiplexing, or data compression techniques offer a solution to the channel count problem for high frequency two-dimensional arrays, but only on the receive side. Transmit remains a difficulty since high voltage drivers for tens of thousands of channels cannot fit in the probe handle, and since an insufficient number of coaxial cables are available to route the transmit signals to the probe from the imaging system.

BRIEF SUMMARY

By way of introduction, the preferred embodiments described below include methods, transducer, and systems for medical imaging, for transducing between electrical and acoustic energies for ultrasound imaging, and/or for volume scanning in ultrasound imaging. The electrodes for a CMUT are split to provide separate transmit and receive bias and alternating current electrodes. The transmit electrodes of different elements are interconnected, such as rows sharing bias and columns sharing transmit alternating signals. The bias is used to select an aperture in elevation, and only a sufficient number of transmit beamformer channels to cover the selected aperture are needed. On receive, the full multi-dimensional array may be used with integrated beamformer electronics.

In a first aspect, an ultrasound transducer is provided for medical imaging. A multi-dimensional array of elements is provided where each of the elements comprises at least one capacitive membrane ultrasound transducer cell having a membrane over a cavity and having at least first and second electrically isolated electrodes on a same side of the cavity. A first electrical interconnection connects the first electrodes along a first direction of the multi-dimensional array such that different elements spaced along the first direction are electrically connected together. A second electrical interconnection connects the second electrodes along a second direction, different than the first direction, of the multi-dimensional array such that different elements spaced along the second direction are electrically connected together.

In a second aspect, a system is provided for transducing between electrical and acoustic energies for ultrasound imaging. A multi-dimensional array of capacitive membrane ultrasound transducer elements is provided. Cells of the elements each have at least first, second and third electrically isolated electrodes. A transmit bias source connects to the first electrodes such that the first electrodes of at least two elements are interconnected. A receive bias source connects to the second electrodes such that the second electrodes of at least two elements being interconnected.

In a third aspect, a method for volume scanning is provided in ultrasound imaging. Transmit beams are generated from a multi-dimensional array of transducer elements with N transmit beamformer channels and M transmit bias channels. Receive beams are generated from the multi-dimensional array of transducer elements with N times M receive beamformer channels.

In a fourth aspect, a method for volume scanning in ultrasound imaging is provided. Transmit beams are generated from a multi-dimensional array of transducer elements with bias selection of a sub-aperture responsive to transmit waveforms. Receive beams are generated with independent operation of the transducer elements.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A split electrode CMUT multi-dimensional array combines a fully sampled M*N element receive matrix with a transmit matrix indexable by overlapping, orthogonal lines. On transmit, M*N acoustic elements can be effectively addressed using M biases generated in the probe handle, and N transmit AC signals. The bias voltages may be generated in the probe handle or the ultrasound imaging system. The transmit AC signals may be supplied by the ultrasound system or generated in the probe handle. On receive, M*N signals are directed to underlying integrated electronics for receive beamformation using all or a large number of elements. A split electrode CMUT design allows these transmit and receive capabilities to be combined in a single device.

An additional advantage of this structure and beamformation technique is that linear transmitters may be used for beamformation, instead of lower quality square wave transmitters. Square wave transmitters require less die area and consume less power than linear transmitters. However, using square wave transmitters instead of linear transmitters degrades contrast resolution in B-mode imaging, and reduces specificity in harmonic and contrast agent imaging. It also precludes the use of chirps and other encoding on transmit. Since the number of transmit channels needed for the multi-dimensional array is limited, linear transmitters in the ultrasound imaging system may be used.

In one example embodiment, a two-dimensional or other multi-dimensional array is formed from CMUT cells. The CMUT cells each have four electrically isolated electrodes—two above and two below the cavity. The first upper electrode extends laterally and the second upper electrode extends longitudinally, each crossing multiple acoustic elements. The first lower electrode runs longitudinally across multiple acoustic elements and has substantial capacitive overlap with portions of the first upper electrode. The second lower electrodes are isolated for each acoustic element and have substantial capacitive overlap with portions of the second upper electrode. The second lower electrodes connect with integrated receive beamformer electronics, allowing independent delaying and/or phasing of each element.

In transmit operation, a first set of DC biases are applied to the first upper electrodes, and a first set of AC signals are established on the first lower electrodes. In receive operation, a second set of DC biases are applied to the second upper electrodes, and a second set of AC signals are measured or detected on the second lower electrodes. N transmit AC channels, M transmit bias channels, and N*M receive channels are used. The transmit focusing is carried out by delaying AC signals in one direction and apodized bias in the orthogonal direction. One or more receive beams are formed via delay and sum of N*M elements on receive.

Figure 1:
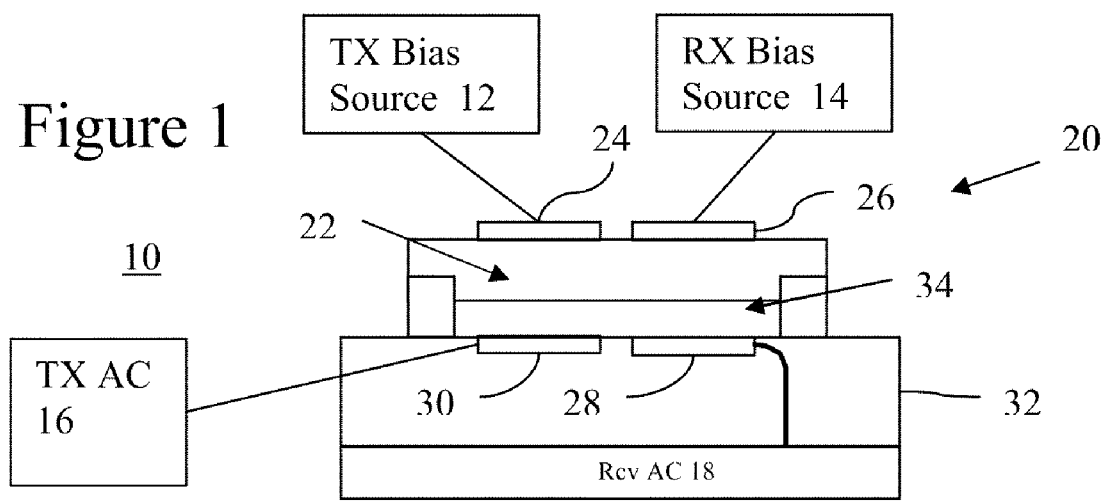
FIG. 1 is a block diagram of one embodiment of a system for transducing between electrical and acoustic energies with a CMUT.

FIG. 1 shows one embodiment of a system 10 for transducing between electrical and acoustic energies for ultrasound imaging. The system 10 includes a transmit bias source 12, a receive bias source 14, a waveform generator 16, a receiver 18, and a CMUT 20. Additional, different or fewer components may be provided. For example, the system 10 is a medical diagnostic ultrasound imaging system and additional components include a detector, scan converter and display for generating ultrasound images. As another example, the CMUT 20 is replaced by a PZT or other transducer. Other arrangements may be provided. For example, the receiver 18 is separate from the CMUT 20. Other ultrasound imaging systems may be provided.

Figure 2:
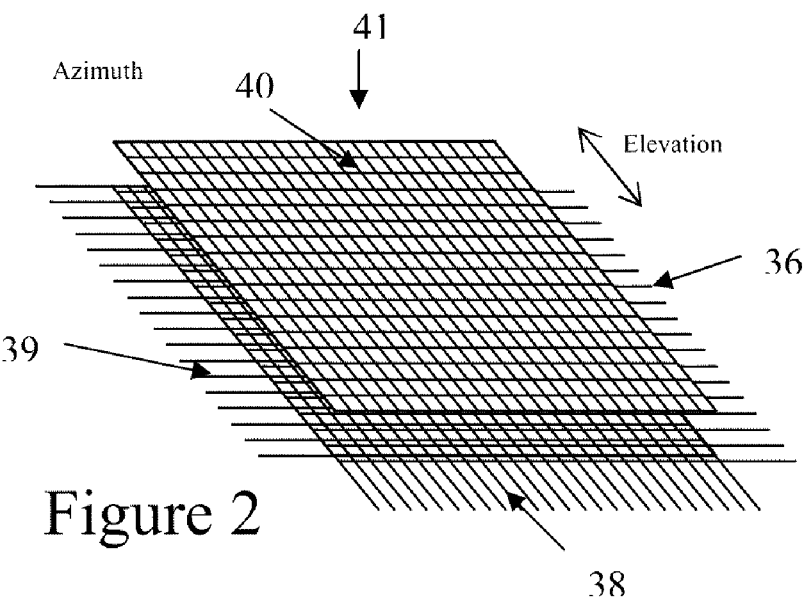
FIG. 2 is a graphical representation showing a electrode interconnection between elements of a multi-dimensional array in one embodiment.

The CMUT 20 is an ultrasound transducer for medical imaging. The CMUT 20 is an array of a plurality of elements. FIG. 1 shows a single cell where one or more cells (e.g., tens or hundreds) are provided for each element. FIG. 2 shows the array 41 with elements 40 in a rectangular grid. Hex, triangular or other grids may be used. Each cell of an element is electrically connected in parallel, and different elements 40 of the array 41 have different electrical connections. The elements 40 are arranged in one of various configurations, such as 1.5 dimensional, two dimensional Cartesian, two dimensional polar, or other multi-dimensional array 41. The array 41, in the example of FIG. 2, has N×M elements 40. For example, 192 rows of elements 40 are provided along the elevation dimension, and 192 columns of elements 40 are provided along the azimuth dimension. Other numbers of elements 40 may be used with spacing for any desired frequency, such as low frequency (e.g., less than 3 MHz), mid frequency (e.g., 3-5 MHz) or high frequency (e.g., greater than 5 MHz). N may or may not be equal. N and M are both greater than one.

The CMUT 20 is a multi-dimensional array 41 of capacitive membrane ultrasound transducer elements 40, but other types of elements may be used. The entire array 41 is on a same substrate 32, but may be formed on different substrates. FIG. 1 shows an example of a CMUT cell of an element 40. Each cell has a membrane 22 over a cavity 34 formed on or in a substrate 32. CMUT cells include any kind of medical ultrasound vibrating acoustic wave transmitters or receivers that use one or more electrostatically charged membranes or structures whose motion is responsive to electrostatic (Coulomb) forces or whose motion results in modulation of electrostatic potential. Such electrostatic transducers include micro-machined, micro-molded or bonded membrane systems used as a transducer. For example, CMUT includes an electrical drivable vibrating micro-diaphragm or membrane 22 made using micro-machining techniques, such as CMOS techniques. The lateral or largest dimension of the diaphragm or membranes may be in the 50 micron range. Any membrane thickness, size, and/or shape may be used, such as rectangular, hexagonal, or circular membranes.

Four electrodes 24, 26, 28, and 30 are provided on each cell. Some or all cells may have fewer or more electrodes, such as three electrodes. At least two electrodes 24, 26, 28, 30 are on opposite sides of the dielectric gap chamber or cavity 34. The electrodes 24, 26, 28, 30 are metal or other conductor separated by an insulator material. The electrodes 24, 26, 28, 30 are electrically isolated from each other. In one embodiment, a plurality of doped silicon membranes 22 acts as one or two electrodes and a doped silicon substrate 32 separated from the membranes 22 act as another one or two electrodes.

The electrodes 24, 26, 28, 30 connect with different components. Transmit and receive functions are delegated to different physical portions of the CMUT membrane 22. Each membrane 22 or cell may have four electrodes: two for the transmit function, and two for the receive function. The electrode 24 is for transmit DC, and the opposing electrode 30 is for transmit AC. The electrode 26 is for receive DC, and the opposing electrode 28 is for receive AC. A same electrode may be used for bias or AC operation in other embodiments.

Figure 3:
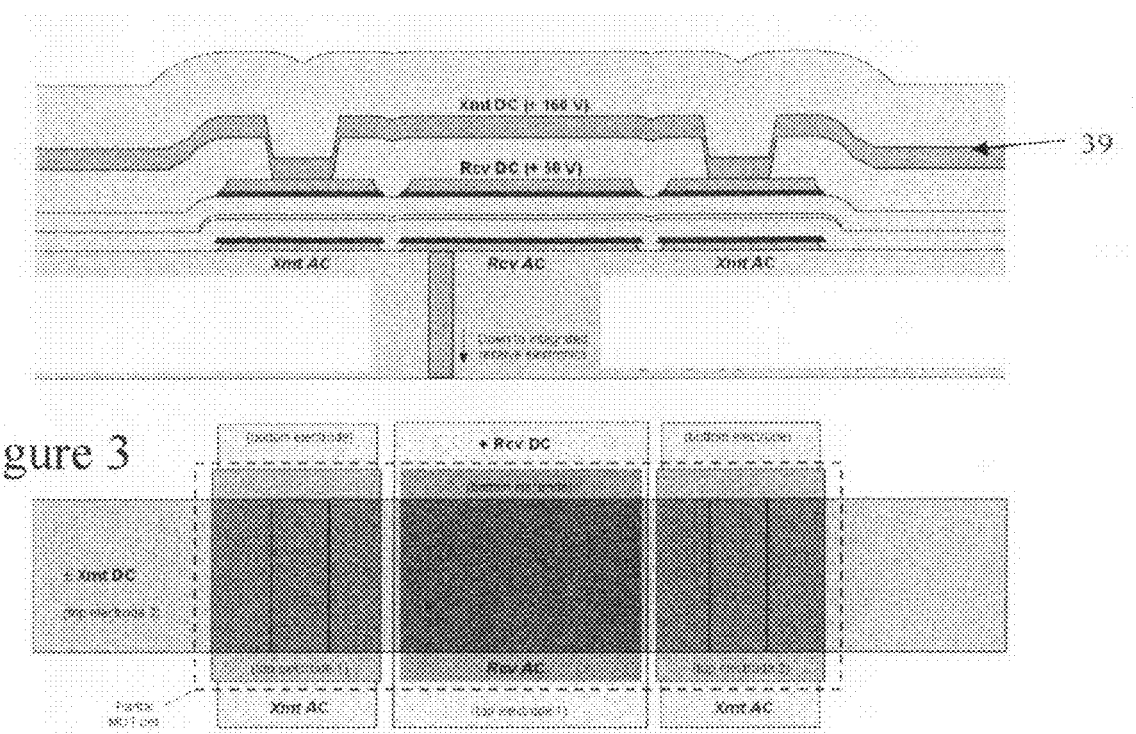
FIG. 3 shows another embodiment of a CMUT structure.

In this design, the CMUT itself is bistatic, with transmit and receive functions carried out on different electrodes. The paired transmit electrodes 24, 30 are on opposite sides of the cavity 34 and substantially overlap in space relative to the direction of acoustic transmission, allowing generating of acoustic energy in response to a changing potential between the transmit electrodes 24, 30. Similarly, the paired receive electrodes 26, 28 are on opposite sides of the cavity 34 and substantially overlap in space relative to the direction of membrane vibration. Any arrangement of electrodes 24, 26, 28, and 30 may be used, such as the ½ and ½ shown in FIG. 1. In another embodiment, the receive electrodes 26, 28 are centered relative to the membrane 22, and the transmit electrodes 24, 30 are positioned at least in part around the receive electrodes 26, 28, along an outer edge of the membrane 22, or closer to the edges of the membrane 22. FIG. 3 shows an example with the transmit electrodes 24, 30 being split on opposite edges of the membrane 22 and the receive electrodes being at the center.

The DC or bias electrodes 24, 26 used for transmit and receive are on a same side of a cavity 34. The AC or signal electrodes 28, 30 are on a same side of the cavity 34, but opposite the bias electrodes 24, 26. In other embodiments, one AC and one DC electrode is provided on the different sides of the cavity 34. Each CMUT cell includes four separate electrodes, two above the vacuum cavity 34 and two below the cavity 34. A field of split electrode CMUT membranes 22 is arranged into 2D acoustic elements.

Figure 4:
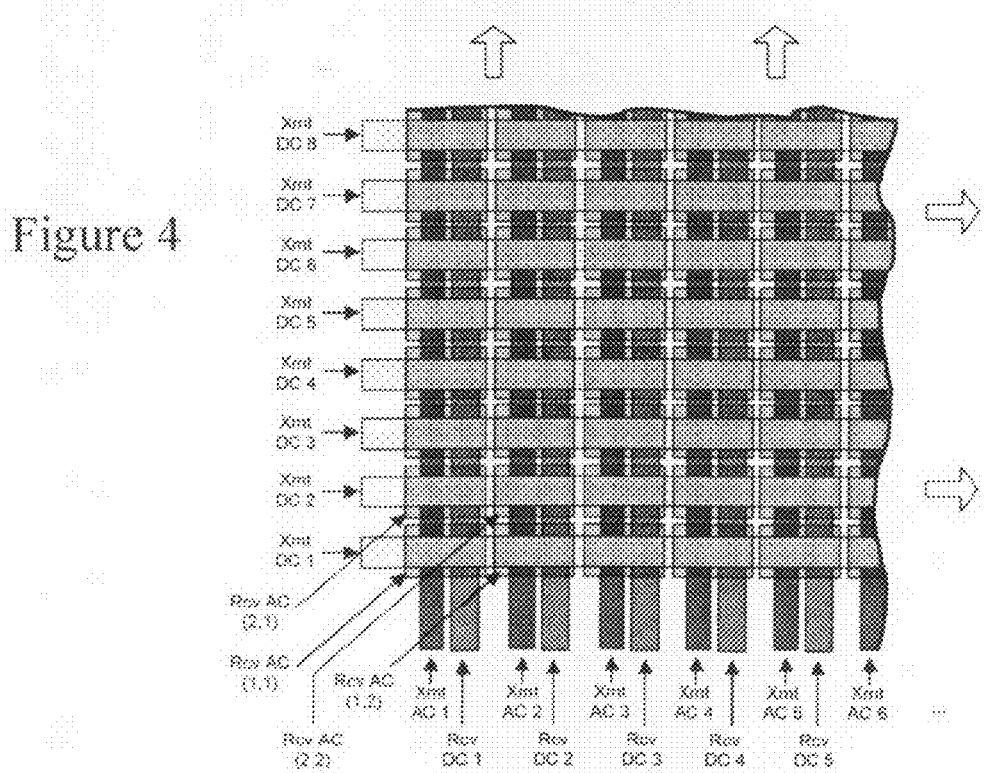
FIG. 4 shows another example embodiment of the electrode interconnection between elements of a multi-dimensional array.

The receive AC electrodes 28 are isolated for each acoustic element 40. The other three electrodes 24, 26, 30 cross over and/or connect to multiple acoustic elements 40 as shown in FIGS. 2-4. The electrodes 24, 26, 30 of different elements 40 are connected together. Two or more elements 40 are interconnected electrically. In one embodiment, the elements 40 along rows or columns in elevation or azimuth are interconnected. The electrical interconnections are traces, conductors, wires, vias, combinations thereof or other now known or later developed electrical paths. FIG. 3 shows the transmit bias connection 39 as a deposited metal layer. The interconnection 39 bridges the other electrodes 26 with an insulation material separating the signal trace and the other electrodes 26.

FIG. 2 shows electrical interconnections 39 connecting elements 40 of each row. The transmit bias electrodes 24 of each row of elements 40 electrically connect to each other. The electrical interconnections 39 extend along the azimuth direction, connecting azimuthally spaced elements 40 together. Different rows are electrically isolated from each other for the transmit bias. In alternative embodiments, the transmit bias electrodes 24 of more than one row of elements 40 are connected together, the interconnections 39 extend less than the entire row, and/or the interconnections 39 connect along other directions (e.g., diagonally or along elevation).

Other electrical interconnections 38 connect elements 40 of each column. The transmit AC or signal electrodes 30 of each column of elements 40 or along a different direction than the bias interconnections 39 connect to each other. The electrical interconnections 38 extend along the elevation direction, connecting elevation spaced elements 40 together. Different columns are electrically isolated from each other for the transmit AC. In alternative embodiments, the transmit AC electrodes 30 of more than one column of elements 40 are connected together, the interconnections 38 extend less than the entire column, and/or the interconnections 38 connect along other directions.

Other electrical interconnections 36 connect the receive bias electrodes 26 of each row or column of elements 40. The interconnections 39 and 36 are shown as parallel in FIG. 2, but may have other arrangements. The interconnections 36, 38, and 39 are electrically isolated from each other. FIG. 2 shows the interconnections 36 and 39 on opposite sides of the array 41, but the connection pads or paths may be exposed or provided on a same side of the array 41.

FIG. 1 shows the electrodes 24, 26, 28, 30 connected to different components. The connections of the bias electrodes 24, 26, and the transmit AC electrode 30 are through the interconnections 36, 38, and 39, but may be direct connections in alternative embodiments.

The transmit bias source 12 is a plurality of potential sources, such as 192 independent bipolar bias generators. In another embodiment, the transmit bias source 12 is a waveform generator, an adjustable DC source, selectable voltage dividers and a voltage source, or other now know or later developed provider of a direct current or slowly variable potential. These generators may switch slowly (e.g., over 50 microseconds) relative to the transmit and receive scan cycle, such as switching between scans for an entire frame of data. The bias applied to different interconnections may be the same between frames, such as switching the bias level for only a few (e.g., 6-12) of the interconnections 39 between each frame.

The transmit bias source 12 connects with the transmit bias interconnections 39, so is electrically connected to the transmit bias electrodes 24. The transmit bias source 12 separately connects with different transmit bias interconnections 39 to supply different bias potential to different groups of elements 40.

The bias voltage circuit allows for two or more selectable bias voltages, such as being an independent waveform generator operable to output a range of different bias voltages. Alternatively, the bias voltage circuit outputs a bias voltage with a few, such as 2, different substantially DC bias voltages. During transmit, the bias voltage establishes an initial position of the membrane 22 of the CMUT 20 pulled partially toward or pushed away from the substrate 32 by electrostatic force. The excitation signal moves the membrane 22 either in or out of the initial position, creating either a rarefaction or compression wave. Higher bias voltages allow for higher possible displacements of the membrane 22. The different bias voltages used for the sequential excitations or transmit events are different in amplitude, polarity, or both amplitude and polarity. For example, positive or negative 160 volt biases are used. Other voltage levels may be used.

The transmit bias source 12 is in the probe handle. Control signals and a power line are provided by the ultrasound imaging system through one or more cables. Alternatively, the transmit bias source 12 is in the ultrasound imaging system and uses a plurality of cables to provide bias potential to the interconnections 39.

The receive bias source 14 is a same or different type of component as the transmit bias source 12. For example, the receive bias source 14 includes 192 non-Zorah bipolar bias generators. The same or different source may be switchably used for both transmit and receive bias. For different sources, some of the circuits may be shared.

The receive bias source 14 connects with the receive bias interconnections 36, so is electrically connected to the receive bias electrodes 26. The receive bias source 12 separately connects with different receive bias interconnections 36 to supply different bias potential to different groups of elements 40.

The receive bias source 14 outputs any desired bias potential, such as 50 Volts. The receive bias is different or the same as the transmit bias. In one embodiment, the transmit bias remains on during receive, such that the receive bias is the provided by the transmit bias source 12 and the receive bias source 14. Differences in polarity of the transmit bias may not affect receive operation. The receive bias may be the same for all elements 40 or may be different for different groups of elements 40. The receive bias may be the same for any imaging or each frame, so may be a constant bias source rather than an adjustable bias source.

During receive operation, the bias voltage establishes a charge on the CMUT capacitance so that incoming pressure waves move the membrane 22 in or out, increasing or decreasing the capacitance. The voltage associated with the capacitance is modulated inversely to preserve the relationship Q=CV. Higher bias provides higher absolute voltage change on the CMUT 20.

The transmit AC source 16 is a transmit beamformer, pulser, switches, transistors, memory, digital-to-analog converter, linear transmitter, arbitrary waveform generator, combinations thereof, or other now known or later developed device for generating an electrical excitation signal. In one embodiment, a plurality of waveform generators connect through transmit channels to a respective plurality of interconnections 38. Each channel includes delays, phase rotators and/or amplifiers for relatively delaying and apodizing excitation signals of each channel relative to other channels. The transmit AC source 16 is operable to generate relatively delayed and/or phased alternating waveforms, such as sinusoidal or square waveforms. The excitation signals have peak-to-peak amplitudes of 100, 200 or other greater or lesser voltages.

The transmit AC source 16 is in the ultrasound imaging system. The imaging system may have sufficient space for 192 or other large number of transmit channels. Cables provide the transmit AC signals to the interconnections 38. In alternative embodiments, the transmit AC source 16 is within the probe housing.

The interconnections 38 provide the transmit waveforms to the groups of elements 40. For example, the different transmit waveforms are provided to respective different columns of elements 40. The elements 40 along each column receive the same transmit waveform. An acoustic beam is formed by propagation of acoustic waves from each of a plurality of elements 40, also activated by the bias, responsive to respectively delayed and apodized excitation signals.

The receive AC circuit 18 is a receive beamformer filter, buffer, processor, circuit or other now known or later developed device for combining signals from different elements 40. For example, the receive AC circuit 18 is a sub-array mixer or time-division multiplexer. As a receive beamformer, the receive AC circuit 18 includes analog or digital channels for applying apodization and relative delays or phasing. The relatively delayed and apodized signals from different channels corresponding to different elements 40 are summed to form a sample representing a given spatial location. By dynamically varying the delays, phasing and/or apodization, samples representing one or more scan lines are generated in a receive event responsive to a given transmit event.

In one embodiment, the summed signals are demodulated to base band. Alternatively, demodulation is performed prior to summation. The demodulation frequency is selected in response to the desired frequency of interest, such as a fundamental or harmonic frequency. Signals associated with frequencies other than mere base band are removed by low pass filtering. As an alternative or in addition to demodulation, band pass filtering isolates the desired information. Using filtering, summation, subtraction or other technique, the receiver AC circuit 18 is operable to isolate information at a desired frequency band.

A switch may be included to disconnect the receiver AC circuit 18 from the electrode 28 during high voltage transmit operation. The receiver AC circuit 18 is integrated in the substrate 32, such as forming at least part of the receiver AC circuit 18 using CMOS processes. For example, one of the sigma-delta based receive beamformers or receivers disclosed in U.S. Published Patent Application Nos. 20070236374 or 20070229336, the disclosures of which are incorporated herein by reference, is integrated, at least in part, in the substrate 32. In alternative embodiments, the receive AC circuit 18 is within the probe housing on a separate substrate and/or circuit board. In other embodiments, the receive AC circuit 18 is, at least in part, in the imaging system, such as a portion of the receive AC circuit 18 integrated in the substrate 32 being a partial beamformer for beamforming subarrays and the remainder of the beamformer being in the imaging system.

The receiver AC circuit 18 connects with the receive AC electrodes 28, such as through one or more vias and/or traces. Each of the elements 40 separately connects to a channel of the receive beamforming electronics. The receive AC electrodes 28 of each element 40 connect with the corresponding receive AC circuit 18. Some of the reflected acoustic energy impinges upon the CMUT 20. In response, the CMUT 20 generates electrical signals. The electrical signals on the receive AC electrodes 28 of an element 40 are provided to the receive AC circuit 18. The receive AC electrodes 28 for each element 40 are electrically isolated from other elements 40 for full beamforming capability.

FIG. 3 shows a via connecting the receive AC electrode (rcv AC) to electronics in the substrate. The electrodes have two transmit AC and DC on the edges of the membrane and the receive AC and DC electrodes being in the middle. The electrodes associated with interconnects are shown extending beyond the partial MUT cell. Partial is used to indicate that the cell and membrane may have a different geometric extent than the electrode arrangement.

FIG. 4 shows one embodiment of an arrangement of interconnections. The interconnections show a single transmit AC, transmit DC, and receive DC for each cell. In other embodiments, such as for the cell structure shown in FIG. 3, two transmit DC and AC electrode pairs are provided for each cell. These pairs share a common electrical connection.

Figure 8A:
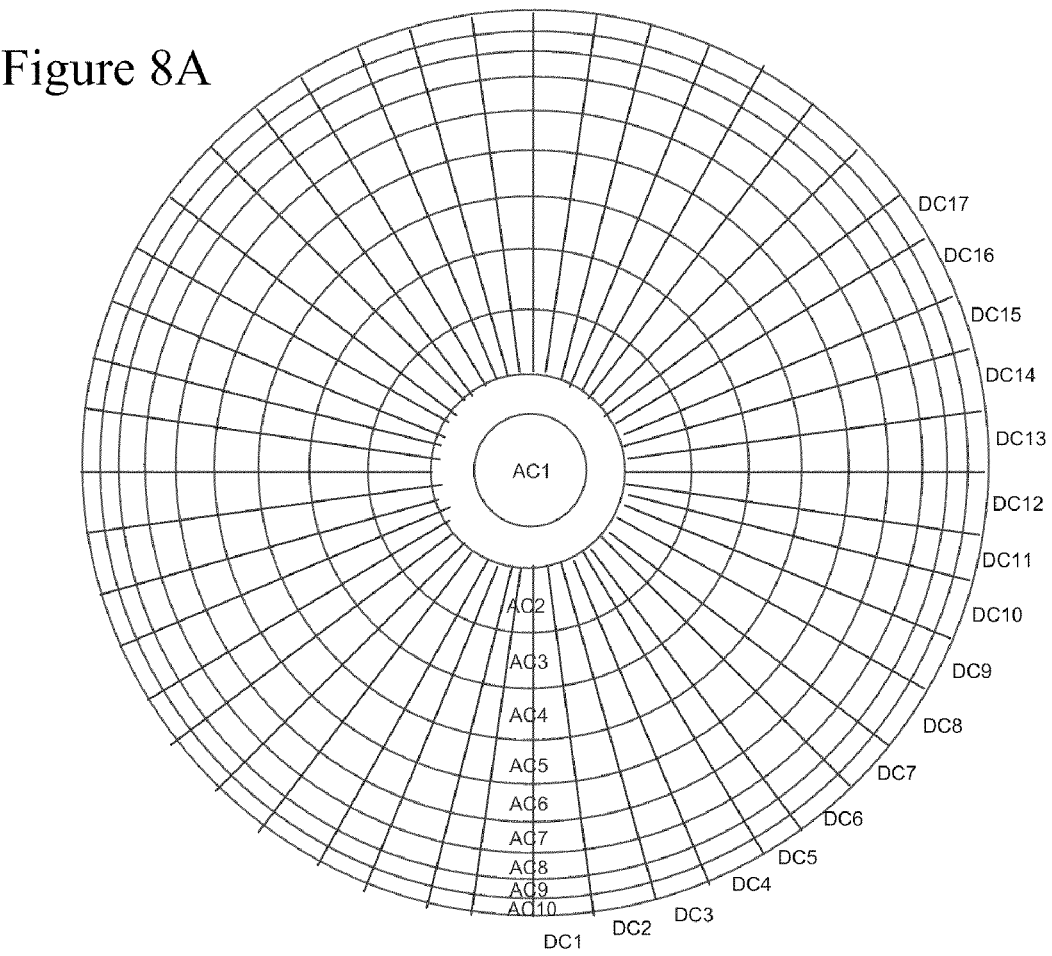
FIGS. 8A-C show an alternative embodiment of electrode interconnection of a multi-dimensional array.
Figure 8B:
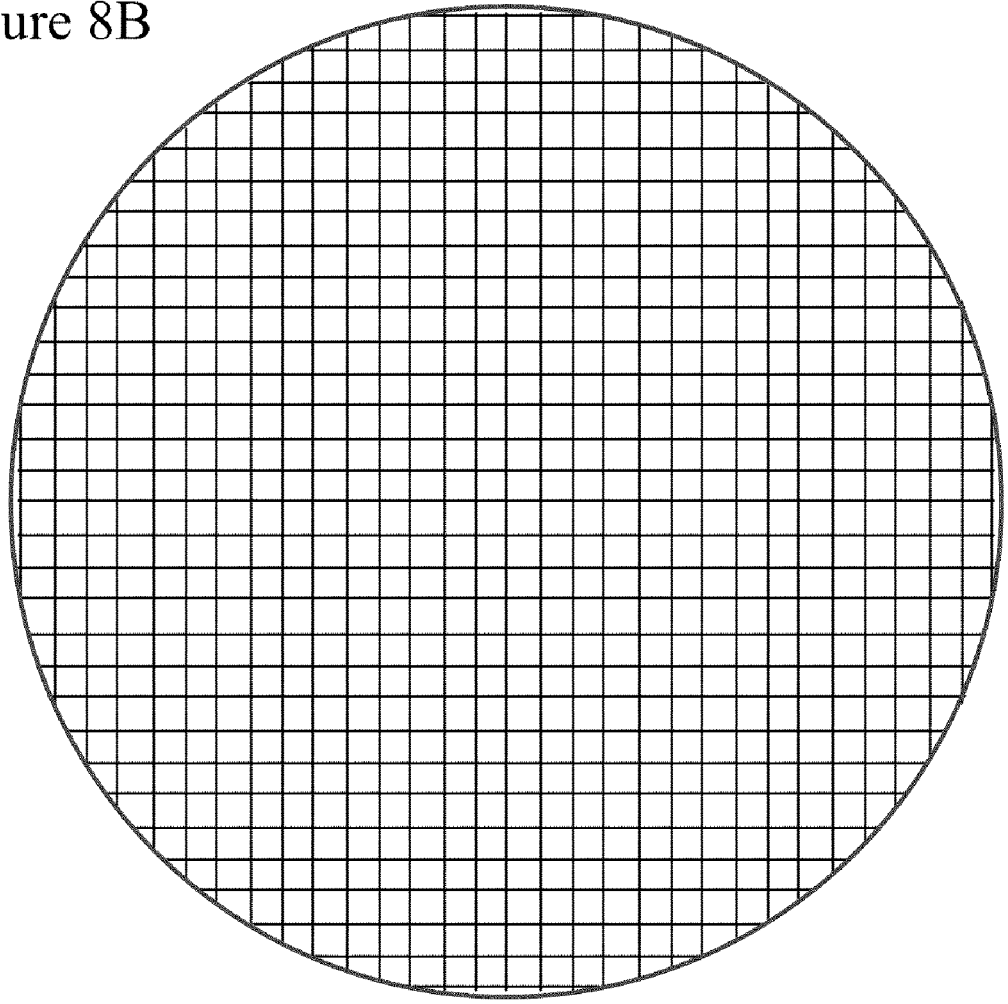
Figure 8C:
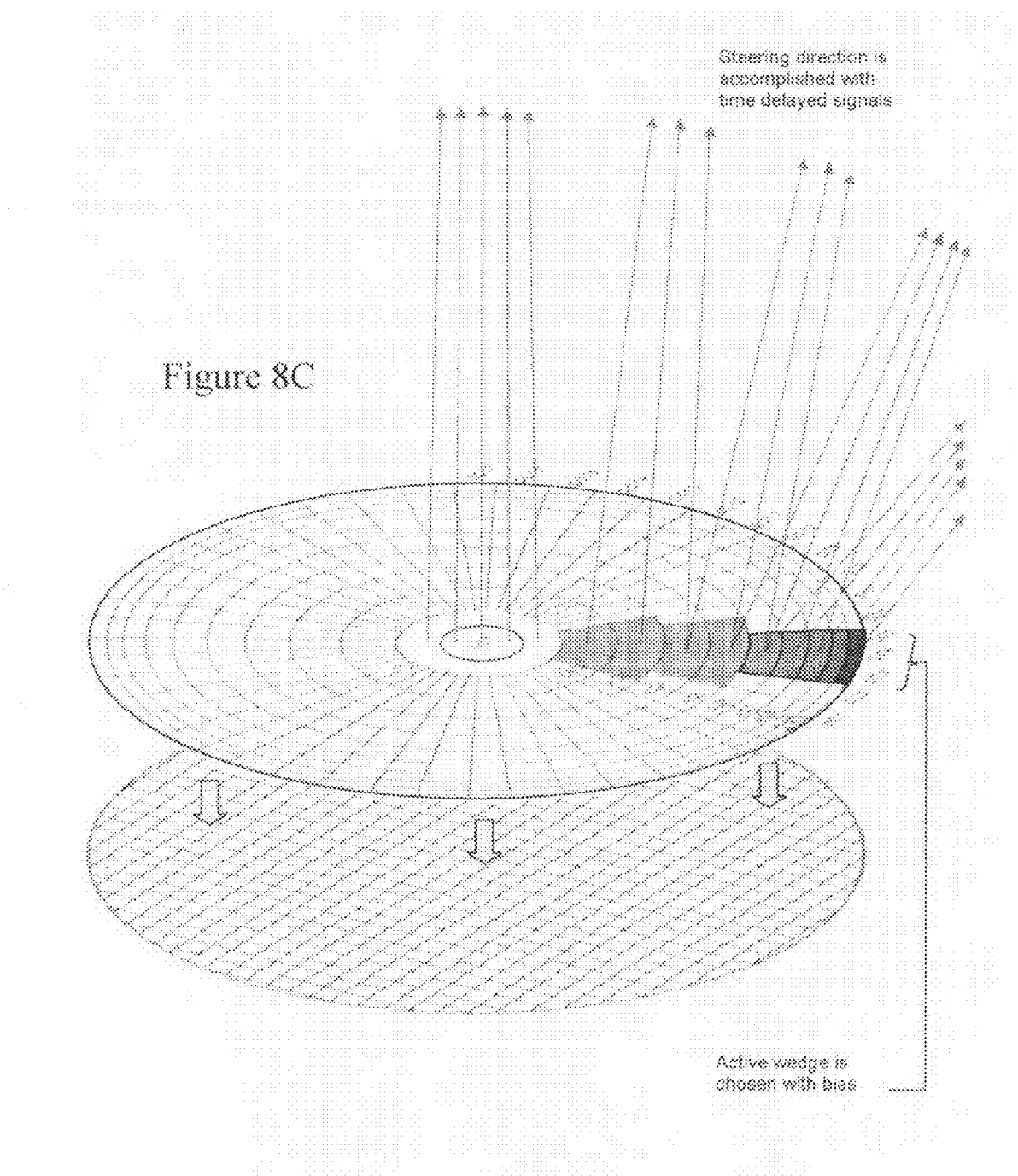

FIGS. 8A-C show an alternative embodiment of an electrode layout for a polar coordinate multi-dimensional array. In FIG. 8A, the relative distribution of the interconnects for transmit is shown. The DC electrode interconnects extend in a radial patter, allowing activation or selection of elements by wedges. The transmit electrode interconnects are circular. FIG. 8B shows the receive electrodes being integrated for independent operation of the elements. FIG. 8C shows transmit operation by selection of a wedge using bias and steering with the selected aperture using the transmit AC interconnects.

Figure 5:
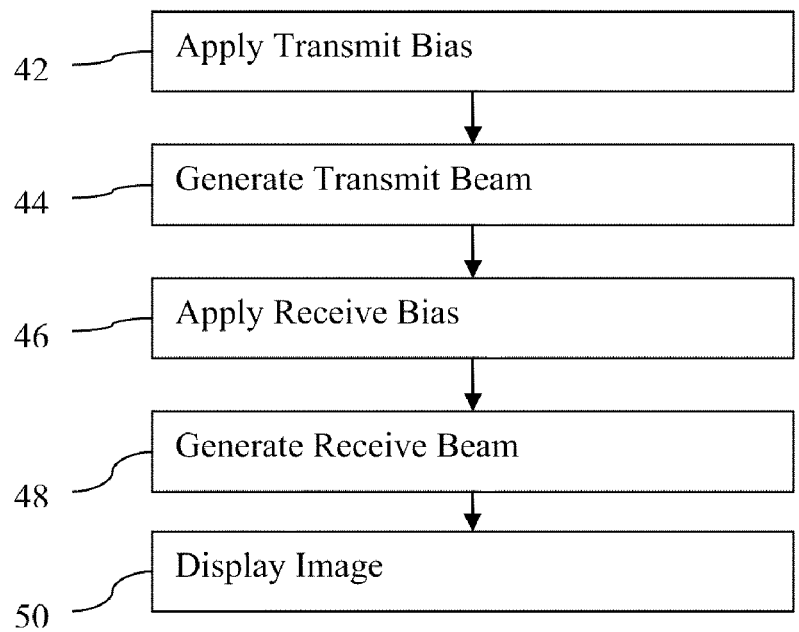
FIG. 5 shows one embodiment of a method for volume scanning with a CMUT multi-dimensional array.

FIG. 5 shows one embodiment of a method for volume scanning in ultrasound imaging. The method is implemented using the system 10 shown in FIG. 1, the array 40 of FIG. 2, the transducer of FIG. 3, the array of FIG. 4, or a different array, transducer, and/or system. Additional, different or fewer acts may be provided than shown in FIG. 5 in the same or different order.

The method is for scanning with a multi-dimensional array of elements, such as an N×M arrangement of the transducer elements. N and M are equal or unequal. The elements transduce between acoustic and electrical energies. For example, CMUT cells use movement of a mechanical structure and corresponding variation in position of electrodes to capacitively transduce. In one embodiment, three or more electrodes are provided for each cell. For example, separate transmit and receive bias electrodes are provided. In another embodiment, separate transmit and receive AC or signal electrodes are provided. Common signal or common bias electrodes may be used. In another embodiment, four electrodes are provided for each cell. The transduction with the elements of the array allows generation of transmit and receive beams.

A transmit beam is formed by transmitting from different elements with relative amplitude, delay, and/or phasing to focus a beam of acoustic energy along a scan line. The beam may be narrow (e.g., for receiving along a single line), broad (e.g., for receiving along two or more scan lines), plane wave, or divergent.

The receive beam is formed by receiving echo signals at different elements. The elements transducer the echo signals into electrical signals. After relative apodization, delay, and/or phasing, the electrical signals are combined to form a receive beam. The receive focus may be dynamic. More than one receive beam may be formed from the same signals, such as by applying different delays and/or phasing to the same signals.

In acts 42 and 44, transmit beams are generated from the multi-dimensional array of transducer elements. To reduce the number of transmit AC signals for a given transmit beam, the bias signals are used to select a sub-aperture responsive to transmit waveforms. Rather than use independent operation of all elements on transmit, the bias determines a sub-aperture along one dimension (e.g., selects rows) and the transmit signals are supplied along another dimension to the selected sub-aperture. For example, the bias selects a limited number of elevation spaced rows (e.g., 12 rows out of 192) for the sub-aperture. Each of the rows has a certain number of elements, such as 192 azimuth spaced elements. Transmit signals are provided to each of the elements, such as 192 transmit signals for the 192 elements in each row. Using the bias sub-aperture selection, transmit beamformation may occur with a limited (e.g., 192) number of transmit beamformer channels.

In act 42, transmit bias signals are applied to the array. The bias signals have the same or different amplitude and/or polarities. The bias signals are applied by row or column, but may be applied in other groupings. The bias signals may turn on or off elements, such as not applying a bias to elements for "off" and applying a bias for "on." In one embodiment, a sub-aperture in a first dimension is selected as a function of the M transmit bias channels. For example, 2-30 groups of elements (e.g., elevation spaced rows) are activated with corresponding positive polarity bias channels. Each of the groups of elements connects with a common one of the M transmit bias channels. For example, M elevation spaced rows are selected for a given transmit event.

The non-selected groups of elements have no bias. Alternatively, the other groups of elements receive varying bias. By applying opposite polarity bias signals to every other group of elements, the signals generated may cancel.

In act 44, the transmit beam is generated by applying transmit signals to the elements. Relatively delayed signals from N transmit beamformer channels are applied along a dimension different than the distribution of bias signals. For example, bias is applied to different rows in elevation. The transmit signals are applied to different columns in azimuth. N elements are provided in each of the M rows of elements activated by the bias signals. CMUTs require both DC bias and AC signal to be acoustically active. On transmit, the aperture is formed out of 2D acoustic elements that lie at the intersection of the active DC bias and AC transmit orthogonal lines.

For each transmit event firing in one embodiment, an F4 or other transmit focus is formed in azimuth by the transmit AC signals. Acoustic energy for the full transmit beam is emitted from a small section of non-alternating bias in elevation. Across the rest of the aperture where the transmit bias alternates from positive to negative, the local transmitted waves cancel in the immediate near field and die out. The pitch of the alternating bias pattern in elevation is chosen such that grating lobes associated with this pattern are pushed out beyond an angle of 90 degrees and do not degrade beam quality. The pitch is determined by the frequency of operation and the electrode pattern. The centerlines of adjacent bias electrodes are selected or positioned to avoid grating lobes.

Figure 6:
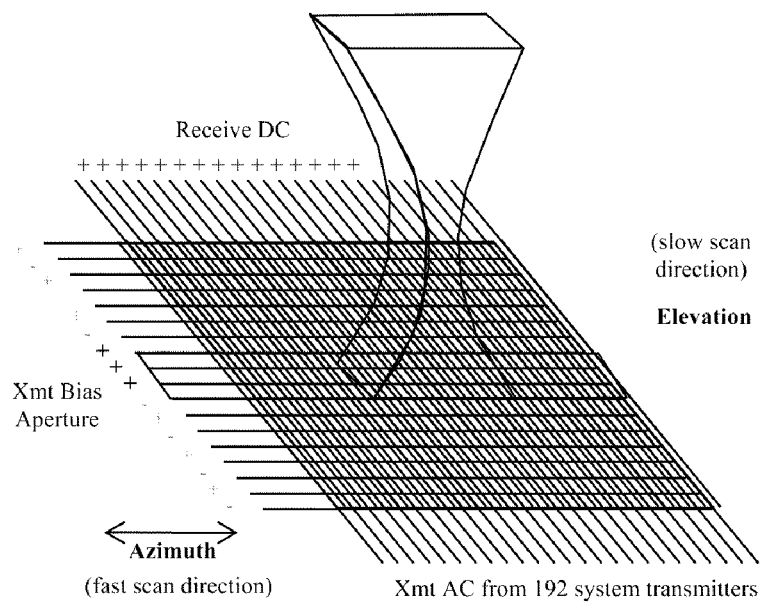
FIG. 6 is a graphical representation of one embodiment of transmit operation.

FIG. 6 graphically represents an example of generating the beam in acts 42 and 44. The hourglass shape generally represents the transmit beam. To achieve target volumetric imaging rates, the transmit beam is partially defocused or is focused to have a width or shape sufficient to cover multiple receive beams (e.g., 6). The transmit beam may be steered in azimuth. In elevation, the position of the transmit beam may shift due to selection of the aperture with bias. The transmit beam is formed to reduce sidelobes and improve contrast resolution. Full sampling of the elements on receive defines point resolution and to further reduces sidelobes.

In acts 46 and 48, receive beams are generated with independent operation of the transducer elements. Full sampling of the array may be provided on receive. In act 46, the elements of the receive aperture are turned on or activated by applying the receive bias. The same bias is applied to all of the elements, but different bias for different groups may be used. A smaller receive aperture than the entire array may be selected by application of the bias. The receive bias may be in addition to the transmit bias applied to the elements at the same time (i.e., during receive).

In act 48, one or more receive beams are generated. While the receive bias is applied, echo signals are transduced into electrical signals for each of the elements of the receive aperture. On receive, all the acoustic elements may be biased and actively convert incoming acoustic energy to electrical signals. For example, a receive beam is generated with a full aperture of the array (e.g., all elements in the array). In other embodiments, a plurality of receive beams are generated in response to echo signals from a single transmit event. For example, with a full aperture of the multi-dimensional array, a plurality (e.g., 4-8 beams) of the receive beams are generated in response to a same transmit beam.

The receive beam or subarray beams for later forming the receive beam are generated with the electronics integrated with the multi-dimensional transducer array. The electrical signals are routed to integrated electronics lying directly below the CMUT cells or elements. The signals are partially or wholly beamformed before being sent to the ultrasound imaging system. On receive, partial beamforming is done on subapertures formed out of multi-dimensional or linear subarrays before the data is sent to the ultrasound system. The imaging system computes six or other number of parallel receive beams (e.g., two beams in azimuth and three beams in elevation) using the partially beamformed data. Alternatively, the receive beam is wholly generated with a receive beamformer in an imaging system. The electronics may multiplex or otherwise combine signals for transmission along a fewer number of cables than elements in the receive aperture.

Figure 7:
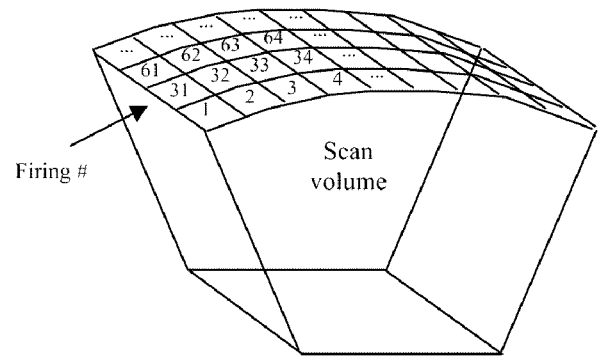
FIG. 7 is a graphical representation of one embodiment of a scan format for volume scanning.

To scan a volume, a plurality of sequential transmit beams and responsive receive beams are generated. Any pattern may be used. FIG. 7 shows one embodiment of a scan pattern. Using bias control, different elevation spaced regions are scanned. Using transmit beamforming in azimuth, different azimuth spaced regions are scanned. The numerical labeling of FIG. 7 represents a sequence of transmit beams where one or more receive beams (e.g., 6—two elevation spaced sets of three azimuth spaced receive beams) are formed in response to each transmission. The elevation spacing between regions in the volume of FIG. 7 is provided by shifting the transmit bias to select a different elevation spaced aperture. A fast volumetric image is made by interrogating a set of adjacent columns extending up from the transducer, scanning first in azimuth, then in elevation. To improve image quality, steered spatial compounding can be implemented in azimuth by firing broad plane waves over a range of 8 or more different angles.

In act 50 of FIG. 5, the beamformed signals are processed for imaging. Information is detected from the beamformed data, such as determining a B-mode (i.e., intensity) value, a velocity estimate, contrast agent response, harmonic response, or other ultrasound detection. The detected information is scan converted into a display format, interpolated to a three-dimensional grid, or processed for three-dimensional imaging without further interpolation. The image may represent a two-dimensional plane through the volume. Alternatively, three-dimensional rendering is performed, such as surface rendering or projection rendering. Grey scale and/or color images are generated.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. An ultrasound transducer for medical imaging, the ultrasound transducer comprising:
   a multi-dimensional array of elements, each of the elements comprising at least one capacitive membrane ultrasound transducer cell having a membrane over a cavity and having at least first and second electrically isolated electrodes on a same side of the cavity, third and fourth electrically isolated electrodes on another same side of the cavity opposite the first and second electrically isolated electrodes;
   a first electrical interconnection connecting the first electrodes along a first direction of the multi-dimensional array such that different elements spaced along the first direction are electrically connected together; and
   a second electrical interconnection connecting the second electrodes along a second direction, different than the first direction, of the multi-dimensional array such that different elements spaced along the second direction are electrically connected together.

2. The ultrasound transducer of claim 1 further comprising integrated beamforming electronics within a substrate, the capacitive membrane ultrasound transducer cells being on or in the substrate, the fourth electrodes connected with the integrated beamforming electronics such that the fourth electrodes for each element are electrically isolated from other elements.

3. The ultrasound transducer of claim 2 wherein the first electrical interconnection connects with a transmit bias source and wherein the second electrical interconnection connects with a receive bias source.

4. The ultrasound transducer of claim 2 wherein the third electrodes connect with a transmit beamformer, the elements in columns connecting to common channels of the transmit beamformer.

5. The ultrasound transducer of claim 1 further comprising a third electrical interconnection connecting the third elements along the first direction of the multi-dimensional array such that different elements spaced along the first direction are electrically connected together.

6. The ultrasound transducer of claim 1 wherein the first electrical interconnection comprises a signal trace bridging over the second electrode at each cell, an insulation material separating the signal trace and the second electrode.

7. The ultrasound transducer of claim 1 wherein the first electrode is along an outer edge of the membrane and the second electrode is at a center of the membrane.

8. The ultrasound transducer of claim 1 wherein the first electrical interconnection connects with a transmit bias source and wherein the second electrical interconnection connects with a receive bias source.

* * * * *